(12) United States Patent
Anderson et al.

(10) Patent No.: US 12,128,100 B2
(45) Date of Patent: Oct. 29, 2024

(54) IMMUNOGENIC COMPOSITIONS FOR TREATMENT OF HEPATITIS B

(71) Applicant: Variation Biotechnologies Inc., Ottawa (CA)

(72) Inventors: David Evander Anderson, Newton, MA (US); Tanvir Ahmed, Ottawa (CA)

(73) Assignee: Variation Biotechnologies Inc., Ottawa (CA)

( * ) Notice: Subject to any disclaimer, the term of this patent is extended or adjusted under 35 U.S.C. 154(b) by 707 days.

(21) Appl. No.: 17/293,431

(22) PCT Filed: Nov. 13, 2019

(86) PCT No.: PCT/IB2019/001230
§ 371 (c)(1),
(2) Date: May 12, 2021

(87) PCT Pub. No.: WO2020/099927
PCT Pub. Date: May 22, 2020

(65) Prior Publication Data
US 2023/0079703 A1    Mar. 16, 2023

Related U.S. Application Data
(60) Provisional application No. 62/760,439, filed on Nov. 13, 2018.

(51) Int. Cl.
| | | |
|---|---|---|
| *A61K 39/00* | (2006.01) | |
| *A61K 38/21* | (2006.01) | |
| *A61K 39/12* | (2006.01) | |
| *A61K 39/29* | (2006.01) | |
| *A61K 45/06* | (2006.01) | |
| *A61P 31/20* | (2006.01) | |
| *A61P 37/04* | (2006.01) | |
| *A61P 43/00* | (2006.01) | |

(52) U.S. Cl.
CPC .......... *A61K 39/292* (2013.01); *A61K 45/06* (2013.01); *A61P 31/20* (2018.01); *A61P 37/04* (2018.01); *A61K 2039/545* (2013.01); *A61K 2039/55505* (2013.01); *A61K 2039/57* (2013.01)

(58) Field of Classification Search
CPC .............. A61K 39/12; A61K 2039/505; A61K 39/292; A61K 2039/57
See application file for complete search history.

(56) References Cited

U.S. PATENT DOCUMENTS

| | | |
|---|---|---|
| 5,242,812 A | 9/1993 | Even-Chen |
| 5,972,346 A | 10/1999 | Hauser et al. |
| 2016/0136264 A1 | 5/2016 | Du et al. |

FOREIGN PATENT DOCUMENTS

| | | |
|---|---|---|
| CN | 1618466 A | 5/2005 |
| CN | 101687029 A | 3/2010 |
| CN | 102949717 A | 3/2013 |
| WO | WO-93/19780 A1 | 10/1993 |
| WO | WO-2018/166298 A1 | 9/2018 |
| WO | WO-2020/099927 A1 | 5/2020 |
| WO | WO-2020/254878 A1 | 12/2020 |
| WO | WO-2020/254878 A8 | 3/2021 |

OTHER PUBLICATIONS

Arico, E. et al., Interferon -? as antiviral and antitumor vaccine adjuvants: mechanisms of action and response signature, J. Int. & Cyt. Res., 32(6):235-247 (2012).
Bertoletti, A. and Gehring, A., Therapeutic vaccination and novel strategies to treat chronic HBV infection, Exp. Rev, Gastro. Hep. 3: 561-569 (2009).
Bertoletti, A. and Rivino, L., Hepatitis B: future curative strategies, Curr Opin Infect. Dis, 27:528-534 (2014).
Bian, Y. et al., Vaccines Targeting PreS1 Domain Overcome Immune Tolerance in HBV Carrier Mice, Hepat., 66:1067-1082 (2017).
Boni, C. et al., Characterization of Hepatitis B Virus (HBV)-Specific T-Cell Dysfunction in Chronic HBV Infection, J. Virol. 81: 4215-4225 (2007).
Clapp, T. et al., Vaccines with Aluminum-Containing Adjuvants: Optimizing Vaccine Efficacy and Thermal Stability, Journal of Pharmaceutical Sciences, 100(2):388-401 (2011).
Dipasquale, A. et al., Vaccine Adjuvants: from 1920 to 2015 and Beyond, Vaccines, 3:320-343 (2015).
Egan, P. M. et al., Relationship between tightness of binding and immunogenicity in an aluminum-containing adjuvant-adsorbed hepatitis B vaccine, Vaccine 27:3175-3180 (2009).
Fazeli, MR. et al., Aluminum phosphate shows more adjuvanticity than Aluminum hydroxide in recombinant hepatitis-B vaccine formulation, DARU 3: 143-148 (2008).
Global Hepatitis Report, World Health Organization, 83 pages (2017).
Grob, P. J. et al., Interferon as an adjuvant for hepatitis B vaccination in non- and low-responder populations, European Journal of Clinical Microbiology; 3:195-198 (1984).
Hansen, B. et al., Effect of the Strength of Adsorption of Hepatitis B Surface Antigen to Aluminum Hydroxide Adjuvant on the Immune Response, Vaccine, 27:888-892 (2020).
Hansen, B. et al., Relationship between the strength of antigen adsorption to an aluminum-containing adjuvant and the immune response, Vaccine, 25:6618-6624 (2007).

(Continued)

*Primary Examiner* — Barry A Chestnut
(74) *Attorney, Agent, or Firm* — Choate, Hall & Stewart LLP; Rolando Medina

(57) ABSTRACT

The present disclosure provides compositions and methods useful for inducing a The cell response in a subject suffering from Hepatitis B. As described herein, the compositions of the disclosure comprise HBsAg having S, Pre-S1 and Pre-S2 proteins and an aluminum phosphate adjuvant. In a preferred embodiment, the immunogenic composition comprises at least 20 μg/ml of HBsAg antigen and the amount of non-adsorbed antigen is at least 30%.

15 Claims, No Drawings
Specification includes a Sequence Listing.

(56) References Cited

OTHER PUBLICATIONS

Helvaci, M. et al., Efficacy of hepatitis B vaccination and interferon-alpha-2b combination therapy versus interferon-alpha-2b monotherapy in children with chronic hepatitis B, J Gast and Hep., 19:785-791 (2004).
Hoa, P. et al., Randomized Controlled Study Investigating Viral Suppression and Serological Response following Pre-S1/Pre-S2/S Vaccine Therapy Combined with Lamivudine Treatment in HbeAg-Positive Patients with Chronic Hepatisis B, Antimicrobial Agents and Chemotherapy, 53(12):5134-5140 (2009).
Hogenesch, H. et al., Optimizing the Utilization of Aluminum Adjuvants in Vaccines, NPJ Vaccines, 3(51):1-11 (2020).
International Search Report for PCT/IB19/01230, 3 pages (mailed Apr. 9, 2020).
International Search Report for PCT/IB20/00539, 5 pages (mailed Nov. 20, 2020).
Iyer, S et al., Mechanism of adsorption of hepatitis B surface antigen by aluminum hydroxide adjuvant, Vaccine, 22:1475-1479 (2004).
Jung, M. C. et al., Immunological monitoring during therapeutic vaccination as a prerequisite for the design of new effective therapies: induction of a vaccine-specific CD4+ T-cell proliferative response in chronic hepatitis B carriers, Vaccine, 20:3598-3612 (2002).
Kaymakoglu, S. et al., Combination Therapy With Hepatitis B Vaccine and Interferon Alfa in Chronic Hepatitis B, AJG, 94:3 856-857 (1999).
Konerman, M. A., et al., Interferon Treatment for Hepatitis B, Clin Liver Dis., 20:645-655 (2016).
Kosinka, A. D. et al., Therapeutic vaccination and immunomodulation in the treatment of chronic hepatitis B: preclinical studies in the woodchuck, Med. Microbial. Immunol, 204:103-114 (2015).
Liaw, Y., HBeAg seroconversion as an important end point in the treatment of chronic hepatitis B, Hepatol Int., 3:425-433 (2009).
Liu, J. et al., New therapeutic vaccination strategies for the treatment of chronic hepatitis B, Virologica, 29: 10-16 (2014).
Lok, A. S. et al., Hepatitis B cure: From discovery to regulatory approval, J. Hep. 67:847-861 (2017).
Mahboubi, A. et al., Comparison of the Adjuvanticity of Aluminum Salts and Their Combination in Hepatisis B Recombinant Protein Vaccine Assessed in Mice, Iran. J. Immunol., 5(3):163-170 (2008).
Miguelina-Colina, M. et al., Recombinant interferon-alpha2b improves immune response to hepatitis B vaccination in haemodialysis patients: results of a randomised clinical trial, Vaccine, 18: 5654-60 (2009).
Milich, D. R. et al., Immune response to the pre-S(1) region of the hepatitis B surface antigen (HBsAg): a pre-S(1)-specific T cell response can bypass nonresponsiveness to the pre-S(2) and S regions of HBsAg, J Immunol 137:315-322 (1986).
Noe, S. M. et al., Mechanism of immunopotentiation by aluminum-containing adjuvants elucidated by the relationship between antigen retention at the inoculation site and the immune response, Vaccine 28: 3588-3594 (2010).
Pol, S. et al., Efficacy and limitations of a specific immunotherapy in chronic hepatitis B, J. Hepatol 34: 917-921 (2001).
Raz, R. et al., Safety and Immunogenicity of a New Mammalian Cell-Derived Recombinant Hepatitis B Vaccine containing Pre-SI and Pre-S2 Antigens in Adults*, IMAJ, 3:328-332 (2001).
Ren, G. et al., Changes in Innate and Permissive Immune Responses after HBV Trasgenic Mouse Vaccination and ILong-Term-si-RNA Treatment, PLOSone, 8(3):e57525 (2013).
Rijckborst, V. et al, The Role of Interferon in Hepatitis B Therapy, Curr Hep. Rep., 9:231-238 (2010).
Rizza, P. et al, IFN -? as a vaccine adjuvant: recent insights into the mechanisms and perspectives for its clinical use, Expert Rev. Vaccines; 10(4); 487-498 (2001).
Shouval, D. et al., Enhanced immune response to hepatitis B vaccination through immunization with a Pre-S1/Pre-S2/S Vaccine, Med Microbiol Immunol., 204:57-68 (2015).
Silva, M O., Risk of autoimmune complications associated with interferon therapy, Gastro & Hepat. 8: 540-542 (2012).
Takemura. F. et al., Complete nucleotide sequence of hepatitis B virus, Nuc. Acid Res, 18(15):4587 (1990).
Vandepapeliere, P et al., Therapeutic vaccination of chronic hepatitis B patients with virus suppression by antiviral therapy: a randomized, controlled study of co-administration of HBsAg/AS02 candidate vaccine and lamivudine, Vaccine 25(51): 8585-8597 (2007).
Vaudin, M. et al., The complete nucleotide sequence of the genome of a hepatitis B virus isolated from a naturally infected chimpanzee, J. Gen Virol., 69(6): 1383-1389 (1988).
Woo, A S. J. et al., Alpha-interferon treatment in hepatisis B, Ann. Transl. Med, 5(7):159 (2017).
Woodell, C. et al., Hepatocyte-targeted RNAi Therapeutics for the Treatment of Chronic Hepatitis B Virus Infection, Mol. Ther. 21: 973-985 (2015).
Written Opinion for PCT/IB19/01230, 5 pages (mailed Apr. 9, 2020).
Written Opinion for PCT/IB20/00539, 10 pages (mailed Nov. 20, 2020).
Yang, D. et al., A mouse model for HBV immunotolerance and immunotherapy, Cell & Mol Bio, 11:71-78 (2014).
Zhao, W et al., Clearance of HBeAg and HBsAg of HBV in mice model by a recombinant HBV vaccine combined with GM-CSF and IFN-? as an effective therapeutic vaccine adjuvant, Oncotarget, 9:34213-34228 (2018).
Zoulim, F. and Durantel, D., Antiviral Therapies and Prospects for a Cure of Chronic Hepatitis B, Cold Spring Harb. Perspect. Med., 5:a21501 (2015).
Hansen, B. et al., Effect of the Strength of Adsorption of Hepatitis B Surface Antigen to Aluminum Hydroxide Adjuvant on the Immune Response, Vaccine, 27:888-892 (2009).
Wang, S. et al., Enhanced type I immune response to a hepatitis B Dna vaccine by formulation with calcium- or aluminum phosphate, Vaccine, 18:1227-1235 (2000).

IMMUNOGENIC COMPOSITIONS FOR TREATMENT OF HEPATITIS B

CROSS REFERENCE TO RELATED APPLICATIONS

The present application is the National Stage of International Application No. PCT/IB2019/001230, filed Nov. 13, 2019, which claims the benefit of U.S. provisional application number 62/760,439, filed on Nov. 13, 2018, the contents of all of which are herein incorporated by reference in their entirety.

SEQUENCE LISTING

The present application contains a Sequence Listing which has been submitted electronically in ASCII format and is hereby incorporated by reference in its entirety. The ASCII copy, created on Oct. 29, 2021, is named 2007801-0146_SL.txt and is 8,506 bytes in size.

FIELD OF THE INVENTION

This invention is in the field of immunogenic compositions, in particular immunogenic compositions useful for treatment of Hepatitis B infection.

BACKGROUND

Hepatitis B is a viral infection which is the causative agent of acute and chronic liver disease. It is transmitted in humans through contact with blood or other body fluids from an infected individual. Hepatitis B infection is a widespread and significant health problem causing chronic liver disease in over 250 million people and close to a million deaths a year worldwide (Global Hepatitis Report 2017, World Health Organization). Upon infection, Hepatitis B causes an acute phase of disease, which has no symptoms in most people. Those who do show symptoms experience jaundice, fatigue and abdominal pain with a small subset of sufferers experiencing acute liver failure which can be fatal. Following infection with Hepatitis B, the patient's immune system may either clear the virus resulting in a cure, or the patient may develop a chronic Hepatitis B infection. The consequences of chronic Hepatitis B are significant, since 30% of chronically infected adults eventually develop cirrhosis and/or liver cancer. The likelihood of developing a chronic disease decreases with age, with infants having a 90% chance of chronic infection, while healthy adults only have a 5%-10% chance.

Although vaccines for Hepatitis B infection have been pursued, a need exists for improved treatments for chronic Hepatitis B patients, particularly treatments that are able to elicit an enhanced cellular immune response in subjects.

SUMMARY

Provided are various embodiments related to immunogenic compositions comprising an HBsAg antigen comprising S, Pre-S1 and Pre-S2 domains and an aluminum phosphate adjuvant, uses of the immunogenic compositions of the disclosure, methods of inducing a Th1 cell response by administering the immunogenic compositions of the disclosure and methods of treating Hepatitis B infection by administering the immunogenic compositions of the disclosure.

In some embodiments, the present disclosure provides an immunogenic composition comprising an HBsAg envelope antigen comprising S, Pre-S1 and Pre-S2 domains (e.g., S, Pre-S1 and Pre-S2 proteins described herein) and an aluminum phosphate adjuvant. In a preferred embodiment, the present disclosure provides an immunogenic composition comprising at least about 20 µg/ml (e.g., at least about 30 µg/ml, at least about 40 µg/ml, at least about 50 µg/ml, or at least about 60 µg/ml) of HBsAg envelope antigen comprising S, Pre-S1 and Pre-S2 domains and an aluminum phosphate adjuvant wherein the amount of unbound antigen is at least 30% (e.g., at least about 35%, at least about 40%, at least about 45%, at least about 50%, at least about 60%, at least about 70%, at least about 80%, or more). In a particularly preferred embodiment, the present disclosure provides a vaccine formulation comprising about 20 µg/ml-60 µg/ml (e.g., about 20 µg/ml, about 30 µg/ml, about 40 µg/ml, about 50 µg/ml, or about 60 µg/ml) of HBsAg antigen comprising S, Pre-S1 and Pre-S2 domains and an aluminum phosphate adjuvant wherein the amount of unbound antigen is at least about 30% (e.g., at least about 35%, at least about 40%, at least about 45%, at least about 50%, at least about 60%, at least about 70%, at least about 80%, or more).

In some embodiments, the immunogenic compositions of the disclosure comprise between 62.5 µg/ml and 500 µg/ml aluminum which is present as aluminum phosphate adjuvant. In a preferred embodiment, the immunogenic compositions of the disclosure comprise 500 µg/ml of aluminum as aluminum phosphate adjuvant. In a particularly preferred embodiment, the immunogenic composition of the disclosure comprises 500 µg/ml of aluminum as aluminum phosphate adjuvant and 20 µg/ml of HBsAg antigen having all three of the S, Pre-S1 and Pre-S2 proteins.

In another embodiment, the present disclosure provides an immunogenic composition for eliciting a Th1 response in a subject, said composition comprising HBsAg envelope antigens comprising S, Pre-S1 and Pre-S2 proteins and an aluminum phosphate adjuvant. In a preferred embodiment, the present disclosure provides an immunogenic composition for eliciting a Th1 response in a mammal, said composition comprising at least 20 µg/ml of HBsAg envelope antigens comprising S, Pre-S1 and Pre-S2 proteins and an aluminum phosphate adjuvant wherein the amount of unbound antigen is at least 30%. In a particularly preferred embodiment, the present disclosure provides an immunogenic composition for eliciting a Th1 response in a mammal, said composition comprising 20 µg/ml-60 µg/ml of HBsAg antigen comprising S, Pre-S1 and Pre-S2 proteins and an aluminum phosphate adjuvant wherein the amount of unbound antigen is at least 30%. In some embodiments, the immunogenic composition for eliciting a Th1 response in a mammal comprises between 62.5 µg/ml and 500 µg/ml aluminum which is present as aluminum phosphate adjuvant. In a preferred embodiment, the immunogenic composition for eliciting a Th1 response in a mammal comprises 500 µg/ml of aluminum as aluminum phosphate adjuvant and 20 µg/ml-60 µg/ml of HBsAg antigen comprising S, Pre-S1 and Pre-S2 proteins. In a particularly preferred embodiment, the immunogenic composition for eliciting a Th1 response in a mammal comprises 500 µg/ml of aluminum as aluminum phosphate adjuvant and 20 µg/ml of HBsAg antigen comprising S, Pre-S1 and Pre-S2 proteins.

In another embodiment, the present disclosure provides an immunogenic composition for treatment of Hepatitis B in a human subject in need thereof, said composition comprising HBsAg envelope antigens comprising S, Pre-S1 and Pre-S2 proteins and an aluminum phosphate adjuvant. In a preferred embodiment, the present disclosure provides an immunogenic composition for treatment of Hepatitis B in a human subject in need thereof, said composition comprising at least 20 µg/ml of HBsAg envelope antigen comprising S, Pre-S1 and Pre-S2 proteins and an aluminum phosphate adjuvant wherein the amount of unbound antigen is at least 30%. In a particularly preferred embodiment, the present disclosure provides an immunogenic composition for treatment of Hepatitis B in a human subject in need thereof, said composition comprising 20 µg/ml-60 µg/ml of HBsAg antigens comprising S, Pre-S1 and Pre-S2 proteins and an aluminum phosphate adjuvant wherein the amount of unbound antigen is at least 30%. In some embodiments, the immunogenic composition for treatment of Hepatitis B in a human subject in need thereof comprises 62.5 µg/ml to 500 µg/ml aluminum which is present as aluminum phosphate adjuvant. In a preferred embodiment, the immunogenic compositions for treatment of Hepatitis B in a human subject in need thereof comprises 500 µg/ml of aluminum as aluminum phosphate adjuvant and 20-60 µg/ml µg/ml of HBsAg antigens comprising S, Pre-S1 and Pre-S2 proteins. In a particularly preferred embodiment, the immunogenic compositions for treatment of Hepatitis B in a human subject in need thereof comprises 500 µg/ml of aluminum as aluminum phosphate adjuvant and 20 µg/ml µg/ml of HBsAg antigens comprising S, Pre-S1 and Pre-S2 proteins.

The present disclosure also encompasses the use of at least one of the immunogenic compositions of the disclosure in the preparation of a pharmaceutical composition intended for treating Hepatitis B infections.

The present disclosure further provides pharmaceutical compositions comprising the immunological compositions of the disclosure for administration to a subject in need thereof.

The present disclosure also provides a method for inducing a Th1 response in a mammal comprising administering a therapeutically effective amount of a composition of the disclosure.

The present disclosure also provides a method for the treatment of Hepatitis B infections, in particular chronic Hepatitis B infection, comprising administering to a subject in need thereof of a therapeutically effective amount of a composition of the disclosure.

In any of the aspects or embodiments described herein, a composition can comprise an S protein (e.g., an S protein comprising or consisting of an amino acid sequence having about 80%, 85%, 90%, 91%, 92%, 93%, 94%, 95%, 96%, 97%, 98%, 99%, or 100% identity to the amino acid sequence of SEQ ID NO:1); a Pre-S2 protein (e.g., a Pre-S2 protein comprising or consisting of an amino acid sequence having at least 80%, 85%, 90%, 91%, 92%, 93%, 94%, 95%, 96%, 97%, 98%, 99%, or 100% identity to the amino acid sequence of SEQ ID NO:2); and a Pre-S1 protein (e.g., a Pre-S1 protein comprising or consisting of an amino acid sequence having at least 80%, 85%, 90%, 91%, 92%, 93%, 94%, 95%, 96%, 97%, 98%, 99%, or 100% identity to the amino acid sequence of SEQ ID NO:3). Embodiments described herein may comprise about 75-90% by weight S protein, about 2-8% by weight Pre-S1 protein, and about 5-15% by weight of Pre-S2 protein (e.g., 83+/−3.3% S protein, 6+/−3% Pre-S1 protein, and 11+/−3% Pre-S2 protein).

Other features, objects, and advantages of the present disclosure are apparent in the detailed description that follows. It should be understood, however, that the detailed description, while indicating embodiments of the present disclosure, is given by way of illustration only, not limitation. Various changes and modifications within the scope of the disclosure will become apparent to those skilled in the art from the detailed description.

LISTING OF SEQUENCES

The following is a list of sequences referred to herein:
SEQ ID NO: 1 is a Small Protein of HBsAG Amino Acid Sequence

```
1           11          21          31
MENITSGFLG   PLLVLQAGFF  LLTRILTIPQ  SLDSWWTSLN 41          51          61          71
FLGGSPVCLG  QNSQSPTSNH  SPTSCPPICP  GYRWMCLRRF 81          91          101         111
IIFLFILLLC  LIFLLVLLDY  QGMLPVCPLI  PGSTTTSTGP 121         131         141         151
CKTCTTPAQG  NSMFPSCCCT  KPTDGNCTCI  PIPSSWAFAK 161         171         181         191
YLWEWGSVRF  SWLSLLVPFV  QWFVGLSPTV  WLSVIWMMWY 201         211         221
WGPNLYNILS  PFIPLLPIFF  CLWVYI
```

SEQ ID NO: 2 is a Medium Protein of HBsAG Amino Acid Sequence

```
1           11          21          31
MQWNSTAFHQ  ALQHPRVRGL  YFPAGGSSSG  TVNPAQNIAS 41          51          61          71
HISSISSRTG  DPAPNMENIT  SGFLGPLLVL  QAGFFLLTRI 81          91          101         111
LTIPQSLDSW  WTSLNFLGGS  PVCLGQNSQS  PTSNHSPTSC 121         131         141         151
PPICPGYRWM  CLRRFIIFLF  ILLLCLIFLL  VLLDYQGMLP 161         171         181         191
VCPLIPGSTT  TSTGPCKTCT  TPAQGNSMFP  SCCCTKPTDG 201         211         221         231
NCTCIPIPSS  WAFAKYLWEW  GSVRFSWLSL  LVPFVQWFVG 241         251         261         271
LSPTVWLSVI  WMMWYWGPNL  YNILSPFIPL  LPIFFCLWVY

281
I
```

SEQ ID NO: 3 is a Large Protein of HBsAG Amino Acid Sequence:

```
MGLSWTVPLE  WGKNQSTSNP  LGFFPDHQLD  PAFGANSNNP

DWDLNSNKDH  WPQANQVGVG  AFGPGFTPPH  GGLLGWSSQA

QGTLHTVPAV  PPPASTNRQT  KRQPTPISPP  LRDSHPQAMQ

WNSTAFHQAL  QHPRVRGLYF  PAGGSSSGTV  NPAQNIASHI

SSISSRTGDP  APNMENITSG  FLGPLLVLQA  GFFLLTRILT

IPQSLDSWWT  SLNFLGGSPV  CLGQNSQSPT  SNHSPTSCPP

ICPGYRWMCL  RRFIIFLFIL  LLCLIFLLVL  LDYQGMLPVC

PLIPGSTTTS  TGPCKTCTTP  AQGNSMFPSC  CCTKPTDGNC

TCIPIPSSWA  FAKYLWEWGS  VRFSWLSLLV  PFVQWFVGLS

PTVWLSVIWM  MWYWGPNLYN  ILSPFIPLLP  IFFCLWVYI
```

DETAILED DESCRIPTION OF THE EMBODIMENTS

The inventors of the present application have made an improved therapeutic Hepatitis B vaccine which is effective at inducing a Th1 cell immune response.

The Hepatitis B virus is a member of the genus *Orthohepadnavirus*, of the *Hepadnaviridae* family of viruses. It is a small, enveloped DNA virus comprising a nucleocapsid and an outer envelope of Hepatitis B surface antigen (HBsAg). The HBsAg antigen is composed of three related envelope proteins that are all encoded by the same open reading frame on the viral DNA (the "S ORF"). These three proteins have the same C terminus but differ at their N-termini due to the presence of three in-frame ATG start codons that divide the S ORF into three regions. The S or "small" envelope protein is the most abundant and the smallest with 226 amino acids. The M or "middle" surface protein includes the S protein and has an extra protein domain consisting of 55 amino acids known as pre-S2. The protein known as the L or "large" protein consists of the S, the Pre-S2 and a third protein domain is known as pre-S1 which has 118 amino acids. The viral genome of Hepatitis B is prone to replication errors, with the result that many genotypes and genetic variants exist. At least ten different genotypes of the virus have been identified, along with many mutations, some of which occur in the S and Pre-S domains. Therefore, many sequence variations exist for each of the three protein domains.

In some embodiments, an S protein described herein comprises or consists of the amino acid sequence of SEQ ID NO:1. In some embodiments, an S protein described herein comprises or consists of an amino acid sequence having at least 80%, 85%, 90%, 91%, 92%, 93%, 94%, 95%, 96%, 97%, 98%, or 99% identity to the amino acid sequence of SEQ ID NO:1. In some embodiments, a Pre-S2 protein described herein comprises or consists of the amino acid sequence of SEQ ID NO:2. In some embodiments, a Pre-S2 protein described herein comprises or consists of an amino acid sequence having at least 80%, 85%, 90%, 91%, 92%, 93%, 94%, 95%, 96%, 97%, 98%, or 99% identity to the amino acid sequence of SEQ ID NO:2. In some embodiments, a Pre-S1 protein described herein comprises or consists of the amino acid sequence of SEQ ID NO:3. In some embodiments, a Pre-S1 protein described herein comprises or consists of an amino acid sequence having at least 80%, 85%, 90%, 91%, 92%, 93%, 94%, 95%, 96%, 97%, 98%, or 99% identity to the amino acid sequence of SEQ ID NO:3.

No effective treatment for Hepatitis B infection has been found. Acute infection is treated with bedrest. Chronic infection is usually treated with antiviral agents, specifically nucleoside-based antiviral agents such as tenofovir, lamivudine, or entecavir or with pegylated interferon alpha (PEG-IFNα). The antiviral agents can slow the progression of cirrhosis and reduce the incidence of liver cancer, but they have proven to be unable to achieve clearance of the virus from the patient. Furthermore, they are costly and they must be continued for the life of the patient to maintain effectiveness. PEG-IFNα is associated with side effects and leads to a sustained antiviral response in only about 30% patients. Accordingly, medicinal treatments for chronic Hepatitis B are generally only effective to slow the progress of the disease, and have not been successful as cures. In order to clear the Hepatitis B virus, and thereby avoid a chronic condition, a patient must generate a potent and diverse immune response. In particular, a strong and specific T cell response is essential to achieving viral clearance of Hepatitis B (Bertoletti and Rivino (2014) Curr Opin Infect. Dis 27:528-534). This type of response is seen almost exclusively in adult patients with mature immune systems (Bertoletti and Gehring, (2013) PLOS Path. 9:1-4).

Given the significant health impact of Hepatitis B infection, much attention has focused on prevention of the disease. Prophylactic vaccines against Hepatitis B have been available for over 30 years and, in many countries, universal vaccination against Hepatitis B is conducted on children. The first prophylactic vaccines against Hepatitis B were developed in the late 1970's using plasma from Hepatitis B patients. Improved Hepatitis B vaccines became available in the 1980's and were produced in yeast cells using recombinant DNA technology to express the S-domain of HBsAg. These more modern vaccines quickly supplanted the first vaccines and are still the principal commercial vaccines on the market today. A more advanced Hepatitis B vaccine was developed in the 1990s, which is produced in mammalian cells and contains all three domains of HBsAg, specifically S, Pre-S1 and Pre-S2. The presence of the Pre-S1 and Pre-S2 domains has been associated with enhanced immunogenic response and, as well, inhibition of viral binding and infectivity (U.S. Pat. No. 5,242,812). The biologic function of the various envelope proteins and the nature of the immune response to each of the components (S, pre-S2, and pre-S1) are only partially understood. However, it is known that, in acute Hepatitis B infection, Pre-S1 and pre-S2 antigens and antibodies appear and disappear early after acute infection, and that antibodies to the S domain appear several weeks later. This, as well as studies using either the Pre-S1 or the Pre-S2 domain antigens, have suggested that the pre-S1 and pre-S2 antigens may be implicated in inducing T-cell help for production of antibodies against the S domain (Milich et al (1985) PNAS 82 8170-8172; Milich et al (1986) J Immunol 137 315-322).

Commercially available prophylactic Hepatitis B vaccines have proven to successfully induce a strong antibody response against the S protein domain of HBsAG in healthy subjects, particularly those who are young and have no impairment to their immune system. However, attempts to use these vaccines as therapeutic treatments in chronic Hepatitis B patients have proved unsuccessful. Clinical trials conducted to measure the therapeutic effect of Hepatitis B vaccines containing the HBsAG S domain alone and the Pre-S2 and S domains together showed that the vaccines were unable achieve clearance of the Hepatitis B virus (Pol et al, (2001) J. Hepatol 34: 917-921). The failure of immunogenic treatment to treat chronic Hepatitis B infection is generally attributed to "immune tolerance", a phenomenon whereby a Hepatitis B patient's immune system becomes unresponsive to further exposure to Hepatitis B antigens, particularly the HBsAg. Immune tolerance in chronic Hepatitis B patients has been associated with the virus' large production of Hepatitis B antigens, which causes exhaustion of T cells, specifically Hepatitis B specific CD8+ T cells (Boni, C. et al, (2007) J. Virol. 81: 4215-4225). Exhausted Hepatitis B specific T cells hyper-express the programmed cell death protein 1 (PD-1) which promotes death of antigen-specific T cells. In patients with high loads of Hepatitis B virus, the destruction of antigen specific T cells can lead to the complete disappearance of these cells from the liver. The result is a weakened T cell response to stimulation by Hepatitis B antigens.

In addition to the challenge presented by immune tolerance, Hepatitis B vaccines containing only the HBsAg S protein may fail to effect clearance of the virus from chronic patients due to their weak ability to stimulate cellular immunity by a T cell response in most subjects. In an effort to more effectively stimulate a T cell response, therapeutic vaccination studies have been carried out in chronic Hepatitis B patients using Hepatitis B vaccines which contain all three of the Pre-S1, Pre-S2 and S protein domains. These studies showed a Hepatitis B specific T cell response in some patients. However, the effect was transient and did not lead to clearance of the disease, possibly because the vaccine stimulated a Th2 response but did not stimulate a CD8+ T-lymphocyte response. (Jung et al, (2002) Vaccine 20: 3598-3612, Kosinka et al (2015) Med. Microbiol. Immunol 204). Th2 cells, characterized by secretion of IL-4, IL-5, and IL-13 cytokines, promote antibody production and are generally associated with allergic responses and are less effective against viral infections than Th1 cells, characterized by secretion of IFN-γ. Further attempts to induce a successful immunological response using DNA vaccines also failed to achieve a sustained response (Bertoletti and Gehring (2009) Exp. Rev, Gastro. Hep. 3: 561-569).

Many researchers have concluded that a complete cure for Hepatitis B is many years away and that, by using a combination of therapies, it may be possible to achieve what has been termed a "functional cure", whereby chronic patients achieve a sustained reduction in Hepatitis B virus and other markers of disease and a reduced incidence of liver cancer following cessation of treatment (Lok et al, (2017) J. Hep. 67:847-861). Due to the failure of antiviral treatments and prophylactic vaccines alone to achieve a functional cure, some researchers have concluded that it may be necessary to combine prophylactic vaccines with Hepatitis B treatments which reduce viral load. Reduction in viral load may reduce the level of immune tolerance and thereby improve the ability of the vaccine treatment to induce an immune response which is able to control the infection (Zoulim, F. et al (2018) Cold Spring Harb. Perspect. Med. (2015): 5: a21501). For example, combinations of prophylactic vaccines with nucleoside inhibitors have been attempted. However, to date, combination therapies using commercially available Hepatitis B vaccines have not succeeded in achieving viral clearance from chronic Hepatitis B patients (Vandepapeliere et al (2007) Vaccine 51: 8585-8597). In a Vietnamese study, an attempt to improve responsiveness was made by combining a newer vaccine, Genhevac B (a Pre-S1, Pre-S2 and S protein vaccine with aluminum hydroxide adjuvant), with a nucleoside inhibitor (lamivudine). This combination was superior to the individual therapies alone in reducing levels of viral DNA in patients. However, the effect was not sustained after the vaccine treatments were discontinued. Accordingly, this combination treatment failed to recruit the patients' immune system to effectively clear the virus (Hoa, (2009) Antimicrob. Agents and Chemo. 53: 5134-5140).

More complex triple combination treatments have been proposed that include an antibody that blocks PD-1 activity along with a nucleoside inhibitor and a prophylactic Hepatitis B vaccine. A study of this triple combination in a woodchuck model using a virus similar to Hepatitis B was effective in only a third of the animals (Kosinka et al, (2015) supra: 103-114; Liu et al, Virologica, (2014) 29: 10-16). Furthermore, the efficacy of this triple combination has not been demonstrated in humans, and it entails the use of costly treatments, possibly indefinitely. Accordingly, the use of conventional prophylactic vaccines for therapeutic purposes, even in combination with other drugs, has not proven successful as a functional cure for Hepatitis B in chronic patients. Therefore, to achieve a sustained response in chronic Hepatitis B patients, improved means must be found to enhance the ability of these patients to mount a T cell response against the virus.

Newer strategies for treatment of chronic Hepatitis B have emerged which utilize gene silencing approaches. Examples of these treatments include the use of small interfering RNA (SiRNA) to interfere with viral gene expression, in particular HBsAg. Like nucleoside inhibitors, these therapies have the potential to reduce viral load and levels of secreted HBsAg (Woodell et al, (2015) Mol. Ther. 21: 973-985) and it has been suggested that they may be useful in combination with treatments that induce an immune response (Ren et al. (2013) PLOSone 8(3):e57525). However, the effectiveness of this combination has not been established and, given the failure of earlier studies with antiviral agents, the effectiveness may depend on the combination including an immunological agent which is capable of stimulating a robust Th1 cell response.

Previous attempts have been made to enhance the T cell response to Hepatitis B vaccines by altering vaccine formulations. Most commercially available Hepatitis B vaccines, including the widely used Hepatitis B vaccine, Engerix B®, and the Hepatitis B vaccine containing S/Pre-S1 and Pre-S2, Sci-B-Vac,® are formulated with aluminum hydroxide adjuvant. Aluminum hydroxide adjuvant is one of a family of aluminum containing adjuvants that are sometimes informally referred to as "alum" (although the word "alum" is more correctly used to describe hydrated potassium aluminum sulfate ($KAl(SO_4)_2.12 H_2O$) which was used as an early adjuvant for diphtheria toxoid but abandoned due to difficulties with manufacturing). Aluminum-based adjuvants have been used in human vaccines since 1932 and, although they have a long record of safety, their mode of action is not completely understood. It is generally believed that aluminum-based adjuvants enhance immune response by activation of dendritic cells.

Studies have been conducted to better understand and enhance the effectiveness of aluminum-based adjuvants. The two most frequently used aluminum-based adjuvants are referred to as "aluminum phosphate" and "aluminum hydroxide", with aluminum hydroxide adjuvant being the most widely used commercially. Aluminum hydroxide adjuvant is not $Al(OH)_3$, but rather crystalline aluminum oxy-hydroxide (AlOOH) which has a larger surface area than crystalline aluminum hydroxide. Aluminum phosphate adjuvant is actually amorphous aluminum hydroxy phosphate ($Al(OH)_x(PO4)_y$) in which some of the hydroxyl groups of aluminum hydroxide adjuvant are replaced by phosphate groups. The surface of aluminum phosphate adjuvant is composed of Al—OH and Al—$OPO_3$ groups. Although they are chemically similar, the two adjuvants have different chemical properties. Aluminum hydroxide adjuvant has a crystalline structure, a large surface area and a positive charge at neutral pH (+30 mVolts). Aluminum phosphate adjuvant is amorphous and has a negative charge at neutral pH (approx. −20 mVolts). Also, aluminum phosphate adjuvant has been shown to dissolve more readily following injection.

Antigens "adsorb" onto aluminum-based adjuvants, meaning that they adhere to the adjuvant forming a layer on the surface. Antigens adsorb onto the surface of aluminum-based adjuvants through electrostatic interaction, van der Waals forces and ligand (principally phosphate) exchange. Ligand exchange is the strongest adsorption force and can occur even when an electrostatic repulsive force is present. HBsAg is largely composed of phospholipids which contain phosphate groups that adsorb strongly to the hydroxylated mineral surface of the adjuvant by ligand exchange between the phosphate groups in the antigen and the surface hydroxyls in the aluminum-based adjuvant. Electrostatic attraction is not the predominant adsorption force for HBsAg (Iver et al, (2004) Vaccine, 22:1475-1479).

Traditionally, adsorption of antigen to aluminum-based adjuvants was intentionally maximized because adsorption was generally thought the be important for immunostimulatory effect due to retention of the antigen at the injection site, creating a "depot" effect with prolonged release of the antigens to the immune system. Moreover, complete adsorption of antigen leads to greater long-term stability of the vaccine formulation during long-term storage. Engerix B® contains 10 µg HBsAg per 250 µg aluminum from aluminum hydroxide adjuvant. This ratio, 0.04 µg HBsAg/µg aluminum, ensures complete adsorption. However, more recently, the relationship between antibody and T cell immunity, efficacy, and adsorption has become less clear. Studies on the effect of the tightness of binding of HBsAg to aluminum hydroxide on antibody production in immunized mice have indicated that the vaccine formulations with the tightest adsorption of the antigen onto the adjuvant yielded the lowest antibody response. (Clapp et al (2011) J. Pharm Sci 100(2) 388-401). One study using the HBsAg S antigen domain showed that aluminum-based adjuvants having a higher phosphate content show decreased adsorption, weaker antigen binding and greater antibody response (Egan et al, (2009) Vaccine 27: 3175-3180). Similarly, a single antigen Hepatitis B vaccine containing aluminum phosphate adjuvant elicited a greater antibody response than a similar vaccine formulated with aluminum hydroxide adjuvant and was effective at a lower adjuvant concentration (Fazeli et al, (2008) DARU 3: 143-148). At least one study has shown that adsorption of antigen by an aluminum-based adjuvant is not required in order for the adjuvant to enhance the antibody response, leading to the conclusion that inflammation and not adsorption is related to immunogenicity (Noe et al, (2010) Vaccine 28: 3588-3594). Little is known about the extent to which altered aluminum compositions and amounts impact Th2 vs. Th1 T cell immunity, though studies reporting higher antibody responses would be assumed by those skilled in the art to have promoted enhanced Th2 but not Th1 responses.

Although aluminum-based adjuvants are well known to improve immunogenicity, it is also well known that they act primarily to enhance antibody production and therefore are most effective at targeting pathogens killed or inhibited through interactions with antibodies. They are generally regarded as ineffective to elicit a Th1 response and rather induce an inflammatory, Th2, response by improving the attraction and uptake of antigen by antigen-presenting cells (APCs). Therefore, aluminum-based adjuvants have not been employed in the search for better stimulants of Th1 cell immunity.

In order to improve the cellular, or "innate" immune response, more modern adjuvants have been added to Hepatitis B vaccines. One such modern adjuvant is the endotoxin, monophosphoryl lipid A (MPL), a bacterial liposaccharide. WO 93/19780, discloses stimulation of T cell responses by HBsAg vaccines with a combination of adjuvants. No T cell response (as measured by IL-2, IFN-γ and IL-4) was observed in Balb/c mice following immunization with HBsAg absorbed on aluminum hydroxide. However, when 3-de-O-acylated monophosphoryl Lipid A (3D-MPL) was added to the formulation, a Th1 cell response was observed (as measured by IL-2 and IFN-γ). A subsequently filed patent by the same research group, U.S. Pat. No. 5,972,346, disclosed improved humoral immunogenicity when aluminum phosphate was used instead of aluminum hydroxide in an HBsAg/3D MPL vaccine formulation. This discovery lead to the development of a commercial vaccine sold under the brand name Fendrix®. Subsequent studies showed that Fendrix elicits a Th1 cellular immune response. However, Fendrix is a costly product, and it has only been approved for use in Europe in patients over 15 years of age suffering from renal deficiency. Furthermore, in other studies, the effects of the 3D-MPL adjuvant have been shown to be short-lived and mostly limited to the site of injection and regional lymph nodes (De Pasquale et al., Vaccine 2015).

More recently, US 20160136264 disclosed a Hepatitis B vaccine consisting of hepatitis B antigen fragments and an adjuvant consisting of immunomodulatory DNA sequences that include CpG motifs which was able to mediate a Th1 response in mice. However, safety concerns have been raised about the use of CpG-based adjuvants in Hepatitis B vaccines and marketing authorization has not be obtained in all jurisdictions.

The inventors of the present application have found that an immunogenic composition comprising of all three HBsAg proteins (S, Pre-S1 and Pre S-2) and an aluminum phosphate adjuvant is effective at stimulating a Th1 cell response in a mammal when the composition has a significant amount of unbound antigen. Physicochemical analysis of the compositions of the disclosure shows that the adjuvant is weakly bound to the HBsAg antigens. As demonstrated further in the Examples herein, this binding is significantly weaker than seen in Hepatitis B vaccines formulated with aluminum hydroxide adjuvant. It is also significantly weaker than seen in formulations comprising HBsAg antigen and aluminum phosphate adjuvant having a lower ratio of HBsAg antigen to aluminum phosphate adjuvant.

Surprisingly, the compositions of the disclosure induced an enhanced Th1 cell response in a mammal without the presence of another, more modern, adjuvant which is known to stimulate cellular immunity such as MPL or CpG. These Th1 cell responses were demonstrated experimentally using different immunological markers, specifically antigen-specific IFN-γ responses and IgG2a/IgG1 ratios. This is surprising in view of previous studies which have shown no Th1 response to conventional Hepatitis B vaccines formulated with aluminum-based adjuvants alone.

Even more surprising, the immunogenic compositions of the disclosure are effective at enhancing Th1 cell responses when a significantly reduced concentration of aluminum phosphate adjuvant was used relative to the amount of antigen in the composition, as compared to a commercially available prophylactic vaccine. In particular, the compositions of the disclosure are effective at enhancing Th1 responses with a 50% lower ratio of aluminum phosphate adjuvant to antigen as compared to the most widely used commercially available prophylactic vaccine.

The vaccines of the disclosure comprise HBsAg which includes all three of the S, Pre-S1 and Pre-S2 proteins. The HBsAg may originate from any genotype, strain or isolate of Hepatitis B. Further, the HBsAg may originate from a native HBsAg or from a modified HBsAg. HBsAg antigen may be isolated from a natural source of Hepatitis B virus such as biological samples (e.g. blood, plasma, sera, semen, saliva, tissue sections, biopsy specimen etc.) collected from an infected subject, cultured cells or tissue cultures. HBsAg may also be produced using recombinant techniques in cells. In some embodiments, HBsAg is expressed in a mammalian cell line. In some embodiments, HBsAg is expressed in Chinese Hamster Ovary cell lines. HBsAg antigen comprising S, Pre-S1 and Pre-S2 domains may be produced using the method disclosed in U.S. Pat. No. 5,242,812. Nucleotide sequences encoding different HBsAg may be found in data banks such as Genbank and in the published literature (for example Fukimori et al (1990) 18 Nuc. Acid Res 4587; Vaudin et al (1988) 69 J. Gen Virol. 1383-1389). An amino acid sequence for the large protein of HBsAg is shown in SEQ ID NO. 1. In a preferred embodiment, the immunogenic compositions of the disclosure comprise 20 µg/ml or more of HBsAg antigen having all three of the S, Pre-S1 and Pre-S2 proteins. In another preferred embodiment, the immunogenic composition of the disclosure comprises 20 µg/ml-60 µg/ml of HBsAg antigen having all three of the S, Pre-S1 and Pre-S2 proteins.

The vaccine formulations of the present disclosure further comprise aluminum phosphate adjuvant. One example of an aluminum phosphate adjuvant suitable for use in the present disclosure is Adju-Phos®, an aluminum phosphate wet gel suspension manufactured by Brenntag.

As shown in Example 2, HBsAg vaccine formulations using aluminum hydroxide adjuvant (including the commercially available, prophylactic formulation of the vaccine containing all three of the S, Pre-S1 and Pre-S2 antigens, sold in association with the trademark Sci-B-Vac) contain less than 5% of non-adsorbed antigen. As shown in Table 3, a formulation containing the same amount of antigen used in the prophylactic vaccine, 10 µg/ml of HBsAg antigen having all three of the S, Pre-S1 and Pre-2 domains, with aluminum phosphate adjuvant rather than aluminum hydroxide did not have an increased amount of non-adsorbed antigen and, in fact, as shown in Table 3, there was no unabsorbed antigen in this formulation. This was surprising because aluminum phosphate adjuvant is known to bind more weakly to HBsAg antigen than aluminum hydroxide adjuvant. Nevertheless, at an antigen concentration of 10 µg/ml of HBsAg, similar levels of adsorption were seen using both the aluminum phosphate adjuvant and the aluminum hydroxide adjuvant.

However, surprisingly, a formulation having an increased concentration of HBsAg antigen (comprising S, Pre-S1 and Pre-S2 proteins) and the same concentration of aluminum phosphate adjuvant demonstrated a substantially increased content of non-adsorbed antigen. An aluminum content of 500 µg/ml from aluminum phosphate adjuvant is equivalent to 2.27 mg/ml of aluminum phosphate adjuvant. At an HBsAg concentration of 20 µg/ml and 500 µg/ml of aluminum present as aluminum phosphate adjuvant, the amount of non-adsorbed antigen was 54.8%. At an HBsAg concentration of 40 µg/ml and 500 µg/ml of aluminum as aluminum phosphate adjuvant, the amount of non-adsorbed antigen was 35.8%. At an HBsAg concentration of 60 µg/ml and 500 µg/ml of aluminum as aluminum phosphate adjuvant, the amount of non-adsorbed antigen was 47.4%. The lowered antigen adsorption was not observed in formulations containing the same HBsAg antigen concentration with aluminum hydroxide adjuvant. In fact, when aluminum hydroxide adjuvant was used, the amount of non-adsorbed antigen remained below 5%, even when the antigen concentration was doubled to 20 µg/ml (see Table 3). Accordingly, the use of aluminum phosphate adjuvant, with an increased HBsAg concentration, resulted in a significant and surprising increase in non-adsorbed antigen.

Accordingly, in a preferred embodiment of the disclosure, the immunogenic composition comprises between 62.5 and 500 µg/ml of aluminum as aluminum phosphate adjuvant. In a particularly preferred embodiment, the immunogenic composition of the disclosure comprises 500 µg/ml of aluminum as aluminum phosphate adjuvant and 20 µg/ml-60 µg/ml of HBsAg antigen having all three of the S, Pre-S1 and Pre-S2 proteins. In a particularly preferred embodiment, the immunogenic composition of the disclosure comprises 500 µg/ml of aluminum as aluminum phosphate adjuvant and 20 µg/ml of HBsAg antigen having all three of the S, Pre-S1 and Pre-S2 proteins.

Using in vivo studies in mice, the inventors of the present disclosure have demonstrated that the immunogenic compositions of the disclosure are effective at enhancing a Th1 response in mice. This effect is unexpected because an enhanced Th1 response was not seen in HBsAg compositions where aluminum hydroxide adjuvant was used, even when the antigen concentration was significantly increased. Specifically, as shown in Example 3, a higher 20 µg/ml concentration of HBsAg antigen (comprising S, Pre-S1 and Pre-S2 proteins) with 500 µg/ml of aluminum as aluminum hydroxide adjuvant did not enhance Th1 T cell immunity in mice compared to the commercially available prophylactic vaccine (which has 10 µg/ml of the same antigen and 500 µg/ml of aluminum as aluminum hydroxide adjuvant). However, as further described in Examples 4 and 5, a preferred immunogenic composition of the disclosure having 20 µg of antigen formulated with 500 µg/ml of aluminum from aluminum phosphate adjuvant elicited a significantly higher Th1 cell response when compared head-to-head with the prophylactic formulation of the vaccine (which has 10 µg/ml of the same antigen and 500 µg/ml of aluminum from aluminum hydroxide adjuvant). Furthermore, as described in Example 6, immunogenic compositions of the disclosure having 20 µs, 40 µg and 60 µg of antigen formulated with 500 µg/ml of aluminum from aluminum phosphate adjuvant all elicited a higher Th1 cell response when compared head-to-head with the prophylactic formulation of the vaccine (which has 10 µg/ml of the same antigen and 500 µg/ml of aluminum from aluminum hydroxide adjuvant). These results indicate that simply altering the adjuvant:antigen ratio in the preferred immunogenic composition of the disclosure was not sufficient to enhance Th1 T cell immunity. Rather, changing both the concentration of antigen and type of adjuvant (aluminum phosphate adjuvant rather than aluminum hydroxide adjuvant) was required to enhance Th1 T cell immunity. Enhanced Th1 immunity was only seen in the compositions having an increased amount of non-adsorbed antigen.

The present disclosure also provides the use of an immunogenic composition of the disclosure for the preparation of a pharmaceutical composition for inducing or enhancing a Th1 cell immune response against Hepatitis B infection in a patient. The present disclosure further provides the use of an immunogenic composition of the disclosure for the preparation of a drug for treating Hepatitis B infection, particularly chronic Hepatitis B infection, in a patient.

The present disclosure also provides pharmaceutical compositions which are useful in therapeutic applications in individuals suffering from chronic Hepatitis B infection.

In certain embodiments, provided pharmaceutical compositions may be formulated for delivery parenterally, e.g. by injection. In such embodiments, formulation may be suitable for intramuscular injection.

In some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, gels, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. Remington's The Science and Practice of Pharmacy, 21st Edition, A. R. Gennaro, (Lippincott, Williams & Wilkins, Baltimore, MD, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure. In some embodiments, pharmaceutical compositions comprise one or more preservatives. In some embodiments, pharmaceutical compositions comprise no preservative.

A pharmaceutical composition in accordance with the disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Pharmaceutical compositions described herein will generally be administered in such amounts and for such a time as is necessary or sufficient to induce or enhance a Th1 immune response in a subject. Dosing regimens may consist of a single dose or a plurality of doses over a period of time. The exact amount of a composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms. In certain embodiments, a particular amount of the vaccine composition is administered as a single dose. In certain embodiments, a particular amount of the composition is administered as more than one dose.

The present disclosure also provides a method of inducing or enhancing a T cell immune response against Hepatitis B infection in a mammal comprising administering to the mammal a composition of the disclosure. The immune response is preferably a Th1 response directed to a Hepatitis B antigen. Administration can be performed by injection by any means, for example by intramuscular injection. Injections can be made with conventional syringes and needles, or any other appropriate devices available in the art.

The present disclosure also provides a method of treating Hepatitis B infection, particularly chronic Hepatitis B infection, in a subject in need thereof comprising administering a therapeutically effective amount of a composition of the disclosure. Administration can be performed by injection by any means, for example by intramuscular injection. Injections can be made with conventional syringes and needles, or any other appropriate devices available in the art.

If desired, a method or use of the disclosure can be carried out in combination with one or more conventional therapeutic treatments for Hepatitis B infection and/or Hepatitis B-mediated disease. Administration of a composition of the disclosure may precede, be concomitant with, or subsequent to the administration of the composition of the disclosure. Therapeutic treatments which may be combined with the compositions of the disclosure may be administered for the purpose of reducing the load of Hepatitis B virus prior to or concomitant with administration of the immunogenic composition of the disclosure. Representative examples of Hepatitis B treatments which may be combined with the compositions of the disclosure include, without limitation, polymerase inhibitors, RNase H inhibitors, nucleoside analogs, nucleotide analogs, TLR agonists, N-glycosylation inhibitors, siRNA, antisense oligonucleotides, anti-hepatitis B antibodies, capsid inhibitors, core protein inhibitors, core assembly modulators, S-antigen reducers or sequesterers including nucleic acid polymers, ccc DNA inhibitors, interferons and immune modulators. Although such standard of care may vary from patient to patient, the most common Hepatitis B treatments include nucleotide or nucleoside analogs (such as lamivudine, entecavir, telbivudine, adefovir, dipivoxil or tenofovir) with or without cytokines (e.g. IFNα, pegylated IFNα2a and pegylated IFNα2b). However, newer treatments for reducing Hepatitis B viral load and/or levels of secreted HBsAg present in the plasma or serum, such as siRNA or S antigen sequestering agents (such as REP-2139, a nucleic acid polymer drug candidate produced by Replicor Inc.), may be effectively combined with the compositions of the disclosure. Hepatitis B treatments can be provided in a single dose or, alternatively, in multiple doses according to standard protocols, dosages and regimens over several hours, days weeks and/or months.

The compositions of the disclosure may also include a further adjuvant.

The invention has been described in an illustrative manner and many modifications and variations of the present invention are possible in light of the above teachings. It is therefore to be understood that within the scope of the claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

EXAMPLES

The following examples describe some exemplary modes of making and practicing certain compositions that are described herein. It should be understood that these examples are for illustrative purposes only and are not meant to limit the scope of the compositions and methods described herein.

Example 1: Preparation of Vaccine Formulations

A Hepatitis B surface antigen consisting of all three of the S, pre-S1 and pre-S2 proteins was prepared in CHO cells in accordance with the method described in U.S. Pat. No. 5,242,812.

Vaccine formulations comprising aluminum hydroxide adjuvant were prepared as follows. Briefly, two different concentrations of HBsAg (10 mcg/ml and 20 mcg/ml) using 500 mcg/ml of aluminum content of aluminum hydroxide adjuvant (Alhydrogel®) were stirred for a time of 16±4 hours at room temperature. More specifically, phosphate sucrose buffer and HBsAg were added to a sterile glass vial and mixed gently with a pipet. To a separate sterile glass vial, a small stir bar was added followed by 0.9% saline and Alhydrogel adjuvant while stirring at 100±50 rpm. While the 0.9% saline and Alhydrogel were stirring, the mixture of PBS and HBsAg was slowly added using a 20-200 μl sized pipette (see Table 1 below). A stopper or leak-proof lid was added to each vial and securely sealed. The Alhydrogel adjuvanted vial was left stirring at room temperature (15-25° C.) for 16±4 hours at 100±50 rpm. Once stirring was completed, the vaccine formulation was stored at 2-8° C. until analysis or immunization.

TABLE 1

Immunogenic Compositions with Aluminum Hydroxide Adjuvant

| | Formulation Volumes | | | | Final Test Article Target Specifications | |
|---|---|---|---|---|---|---|
| Final HBsAg Concentration (µg/mL) | Volume of sterile PBS (µL) | Volume of 10 µg/ml HBsAg (µL) | Volume of 0.9% (154 mM) Sodium Chloride (µL) | Volume of 2% Alhydrogel (10 mg/mL Al+++) (µL) | Final Volume (µL) | Final Aluminum Concentration (µg/mL Al+++) |
| 20 | 219 | 181 | 3400 | 200 | 4000 | 500 |
| 10 | 309 | 91 | 3400 | 200 | 4000 | 500 |

Vaccine formulations comprising aluminum phosphate adjuvant (Adjuphos®) were prepared as follows. Briefly, two different concentrations of HBsAg (10 µg/ml and 20 mcg/ml) using 500 µg/ml of aluminum as aluminum phosphate adjuvant (Adjuphos) was rotated at 8-12 rpm for 60 minutes at room temperature. More specifically, Adjuphos adjuvant was added to a sterile container followed by a 10 mM phosphate 8% sucrose buffer. HBsAg was added to the same container and mixed slowly by aspirating pipette (see Table 2 below). The container was sealed and covered with aluminum foil, and then rotated for 60 minutes at 8-12 rpm at room temperature. Once stirring was completed, the vaccine formulation were stored at 2-8° C. until analysis or immunization.

TABLE 2

Immunogenic Formulations with Aluminum Phosphate Adjuvant

| Final HBsAG Concentration (µg/mL) | Volume of 10 mM Phosphate Buffer, 8% Sucrose (µL) | Volume of HBsAg (µL) | Volume of 2% AdjuPhos (5 mg/mL Al+++) (µL) | Final Volume (µL) | Final Aluminium Concentration (µg/mL) |
|---|---|---|---|---|---|
| 60 | 0 | 9000* | 3000 | 30000 | 500 |
| 40 | 3000 | 6000* | 3000 | 30000 | 500 |
| 20 | 3619 | 181** | 200 | 4000 | 500 |
| 10 | 3709 | 91** | 200 | 4000 | 500 |

*HBsAg (Concentration = 200 µg/mL; Lot# B-061-6 diluted),
**HBsAg (Concentration = 441 µg/mL; Lot# B-054-3), Example 2: Evaluation of Adsorption of Antigen to Adjuvant Binding of Hepatitis B surface antigen to aluminum hydroxide adjuvant and aluminum phosphate adjuvant was measured as follows. Briefly, within a sterile biosafety cabinet, 500 µL of each vaccine formulation was aseptically transferred into a sterile polypropylene centrifuge tube, after mixing 10-20 times by pipetting prior to transferring to assure the solution was homogenous. All aliquots were then centrifuged at 14,000 g for 120 minutes. Supernatant (450 µl) was carefully removed from the centrifuged tubes containing the immunogenic formulations using a 20-200 µL pipette and transferred into new, sterile polyprophylene centrifuge tubes. The centrifuged tubes containing pellets of immunogenic formulation were resuspended by addition of a volume of buffer equal to that removed (450 µl). Tubes were labelled appropriately (supernatant vs. resuspended pellets of centrifuged immunogenic formulations). Diluted pellets (containing bound HBsAg) and supernatants (containing free HBsAg) were stored at 2-8° C. in a fridge. Table 3 below demonstrates the impact of HBsAg antigen concentration, choice of aluminum adjuvant, and adjuvant dose on the amount of unbound/free HBsAg.

TABLE 3

Non-Adsorbed Antigen Content of Test HBsAg Compositions

| Test Article | Target HBsAg (µg/mL) | Target Aluminum µg/mL [Al+++] | Total Protein (µg/mL) | | | Non-adsorbed HBsAg |
|---|---|---|---|---|---|---|
| | | | Original | Supernatant (Free) | Pellet (Bound) | |
| 1 | 40 | 62.5 Alhydrogel | 31.9 | 0.8 | 32.1 | 2.8% |
| 2 | 40 | 125 Alhydrogel | 33.2 | Not Detected | 35.8 | 0% |
| 3 | 40 | 250 Alhydrogel | 41.6 | 1.1 | 39.6 | 2.7% |
| 4 | 40 | 500 Alhydrogel | 44.8 | 1.2 | 47.6 | 2.5% |
| 5 | 20 | 500 Alhydrogel | 39.8 | Not Detected | 36.6 | 0% |
| 6 | 10 | 500 Alhydrogel | 32.5 | Not Detected | 34.3 | 0% |
| 7 | 40 | 62.5 Adjuphos | 10.2 | 5.9 | 4.9 | 54.6% |
| 8 | 40 | 125 Adjuphos | 10.1 | 5.1 | 4.2 | 54.8% |
| 9 | 40 | 250 Adjuphos | 10.5 | 4.5 | 5.2 | 46.4% |
| 10 | 40 | 500 Adjuphos | 12.2 | 3.8 | 6.8 | 35.8% |
| 11 | 20 | 500 Adjuphos | 10.0 | 3.4 | 2.8 | 54.8% |
| 12 | 10 | 500 Adjuphos | 3.5 | Not Detected | 3.1 | 0% |
| 13 | 60 | 500 Adjuphos | 11.84 | 7.6 | 8.43 | 47.4% |

Test article 6 (TA6) is the commercially available, prophylactic Sci-B-Vac vaccine and there was no detectable non-adsorbed (free) HBsAg that could be detected in the supernatant. Changing the ratio of antigen to adjuvant by increasing the antigen concentration 4-fold (TA4) did not substantially change the amount of non-adsorbed antigen (2.5%). Similarly, changing the ratio of antigen to adjuvant by reducing the amount of aluminum hydroxide adjuvant (Alhydrogel) did not increase the amount of non-adsorbed antigen above 5% (TA1-3).

Changing the adjuvant used in the immunogenic compositions from aluminum hydroxide adjuvant (Alhydrogel) (TA6) to aluminum phosphate adjuvant (Adjuphos) (TA12) similarly failed to increase the amount of non-adsorbed HBsAg (0% detected) when the concentration of HBsAg was kept at 10 µg/ml. Surprisingly, however, increasing the concentration of antigen (TA11) 2-fold and/or decreasing the concentration of aluminum phosphate adjuvant (TA7-10) substantially increased the amount of non-adsorbed HBsAg to above 30%. In particular, a 20 µg/ml concentration of antigen demonstrated a very high amount of non-absorbed HBsAg when formulated with 500 µg/ml of aluminum from aluminum phosphate adjuvant. This adjuvant concentration, specifically 500 µg/ml, is widely used in commercially available HBsAg vaccines, albeit with aluminum hydroxide adjuvant rather than aluminum phosphate adjuvant.

In summary, there is no non-adsorbed HBsAg in the commercially available prophylactic vaccine known as Sci-B-Vac (TA6) but greater than 50% of non-adsorbed HBsAg in an embodiment of the disclosure having 20 µg/ml HBsAg and 500 µg/mL aluminum as aluminum phosphate adjuvant (TA11). Changes in both the type of aluminum-based adjuvant and the concentration of antigen were necessary to obtain amounts of non-adsorbed antigen greater than 30%.

Example 3: Evaluation of Th1 T Cell Immunity in Mice after Vaccination with Two Different Immunogenic Compositions Comprising HBsAg Comprising S, Pre-S1 and Pre-S2 and Aluminum Hydroxide Antigen This Example describes evaluation of T cell response in mice following immunization with two different immunogenic formulations comprising different concentrations of antigen (HBsAg comprising S, Pre-S1 and Pre-S2 protein) and 500 µg/ml of aluminum from aluminum hydroxide adjuvant (TA5 and TA6 in Table 3). Balb/c mice were vaccinated 3 times on week 0, 3, 10 (or 13) with 1/20th of the human dose formulations of vaccine (i.e. 0.5 µg of antigen of TA6 and 1.0 µg of antigen of TA5). Mice were sacrificed on day 6 post $3^{rd}$ vaccination to measure responses to the pre-S1, pre-S2, and HBsAg S proteins using overlapping peptide pools by enzyme linked immunospot assay ("ELISPOT") as described below. Comparable anti-HBsAg antibody responses were induced with the two formulations (data not shown).

IFN-γ ELISPOT analyses to measure Th1 T cell responses were performed as follows. Mice were split into groups of 8 mice each immunized with the two test formulations described above, each having the same concentration of aluminum hydroxide adjuvant but different concentrations of HBsAg antigen. Four mice per group were sacrificed and spleens were removed. Spleens from individual mice were processed to produce single cell suspensions. Erythrocytes were lysed using a commercially available buffer (BioLegend). Splenocytes were then re-suspended at $6\times10^6$ splenocytes/mL. One day prior to spleen collection and processing, ELISPOT plates were coated with Interferon-gamma (IFN-γ) capture antibody. No peptide, actin peptide mix, Pre-S1 peptide mix, Pre-S2 peptide mix, HBsAg peptide mix, and phorbol 12-myristate 13-acetate and ionomycin (PMA/iono) were selected as stimulants. On the day of the spleen collection, stimulants were added to designated ELISPOT plate wells. $1.5\times10^5$ splenocytes were added to PMA/iono wells and $3\times10^5$ splenocytes were added to all other stimulants. The ELISPOT plates were then placed into a humid 37° C. with 5% CO2 incubator for 40-48 hours. After incubation, the plates were washed for removal of splenocytes, stimulants and media and IFN-γ capture antibody was added, followed by streptomycin horseradish peroxidase (strep-HRP). The plates were finally developed with commercially available 3-Amino-9-ethylcarbazole (AEC) substrate (BD BioSciences). The observed spots were counted using an ELISPOT plate reader and the final data was reported as spot forming cells (SFC) per one million splenocytes. Table 4 below presents the results of this immunogenicity study.

TABLE 4

| | Th1 Activity as measured by ELISPOT | | | | | |
|---|---|---|---|---|---|---|
| | Pre-S1 (IFN-γ + SFC/10$^6$ splenocytes) | | Pre-S2 (IFN-γ + SFC/10$^6$ splenocytes) | | sAg (IFN-γ + SFC/10$^6$ splenocytes) | |
| Immunogenic Composition | GM | SE | GM | SE | GM | SE |
| 10 µg HBsAg Formulation containing 500 µg/mL [Al+++] (Alhydrogel) | 6.048 | 2.549 | 124.6 | 38.31 | 1056 | 225.9 |
| 20 µg HBsAg Formulation containing 500 µg/mL [Al+++] (Alhydrogel) | 6.328 | 2.918 | 112.3 | 48.17 | 1094 | 214.6 |

Note:
GM = Geometric mean;
SE = Standard Error

Table 4 demonstrates that higher amounts of HBsAg antigen in formulations containing aluminum hydroxide as the adjuvant did not show improved Th1 T cell response. This result is consistent with the data in Table 2, which showed that both formulations had no non-absorbed antigen.

Example 4: Comparison of T Cell Immunity in Mice Following Vaccination with a Commercially Available Prophylactic Vaccine Known as Sci-B-Vac (10 µg/ml HBsAg Comprising S, Pre-S1 and Pre-S2 and 500 µg/ml Aluminum as Aluminum Hydroxide Adjuvant) and a Formulation of the Disclosure Comprising 20 µg HBsAg and 500 µg/ml Aluminum as Aluminum Phosphate Adjuvant.

This Example describes evaluation of T cell response in mice following vaccination with two different immunogenic compositions. The first composition was the commercially available prophylactic vaccine known as Sci-B-Vac which comprises 10 µg/ml HBsAg comprising S, Pre-S1 and Pre-S2 proteins and 500 µg/mL aluminum as aluminum phosphate adjuvant (TA6 in Table 3). The second composition was an immunogenic composition of the disclosure comprising a 2-fold higher concentration of the same HBsAg (20 µg/ml) and 500 µg/mL aluminum as aluminum phosphate adjuvant (TA11 in Table 3). Balb/c mice were vaccinated 3 times on week 0, 3, 6 (or 8) with ½0th of the human dose of each immunogenic composition (i.e. 0.5 µg of antigen of TA6 and 1.0 µg of antigen of TA11). Mice were sacrificed on day 6 post 3$^{rd}$ vaccination to measure responses to the pre-S1, pre-S2, and HBsAg proteins using overlapping peptide pools by ELISPOT as described above. Comparable anti-HBsAg antibody responses were induced with the two formulations.

TABLE 5

Th1 Activity as measured by ELISPOT

| Immunogenic Composition | Pre-S1 (IFN-γ + SFC/10⁶ splenocytes) | | Pre-S2 (IFN-γ + SFC/10⁶ splenocytes) | | sAg (IFN-γ + SFC/10⁶ splenocytes) | |
|---|---|---|---|---|---|---|
| | GM | SE | GM | SE | GM | SE |
| 10 µg HBsAg Formulation containing 500 µg/mL[Al+++] (Alhydrogel) | 5.833 | 0.4951 | 53.66 | 7.991 | 160.3 | 35.78 |
| 20 µg HBsAg Formulation containing 500 µg/mL[Al+++] (Adjuphos) | 5.439 | 0.8325 | 271.7 | 62.9 | 333.0 | 35.51 |

As can be seen from Table 5, the immunogenic composition of the disclosure containing 20 µg HBsAg and 500 µg/ml aluminum as aluminum phosphate adjuvant stimulates a substantially greater Th1 cell response against the Pre-S2 and S antigens than does the commercially available prophylactic version of the vaccine formulated with a much lower concentration of the same antigen (10 µg/ml) and aluminum hydroxide adjuvant. This result is consistent with the data in Table 2 which shows a large percentage of non-bound antigen (54.8%) in the immunogenic composition of the disclosure (TA11) as compared to no unbound antigen in the commercially available prophylactic HBsAg vaccine (TA6). The response appears to have been greatest with respect to Pre-S2. No responses were detected against the preS1 antigen with either formulation.

Example 5: Comparison of Individual IgG1/IgG2a Ratios in Mice Following Vaccination with a Commercially Available Prophylactic Vaccine Known as Sci-B-Vac (10 µg/ml HBsAg Comprising S, Pre-S1 and Pre-S2 and 500 µg/ml Aluminum as Aluminum Hydroxide Adjuvant) and a Formulation of the Disclosure Comprising 20 µg HBsAg and 500 µg/ml Aluminum as Aluminum Phosphate Adjuvant This Example describes comparison of individual IgG1/IgG2a ratios in mice following vaccination with two different immunogenic compositions. The first composition was the commercially available prophylactic vaccine known as Sci-B-Vac which comprises 10 µg/ml HBsAg comprising S, Pre-S1 and Pre-S2 proteins and 500 µg/mL aluminum as aluminum hydroxide adjuvant (TA6 in Table 3). The second composition was an immunogenic composition of the disclosure comprising a 2-fold higher concentration of the same HBsAg (20 µg/ml) and 500 µg/mL aluminum as aluminum phosphate adjuvant (TA11 in Table 3). Balb/c mice (n=8) were vaccinated 3 times on weeks 0, 3, 6 with ½0th of the human dose of each immunogenic composition (i.e. 0.5 µg of antigen of TA6 and 1.0 µg of antigen of TA11). Mice were sacrificed on day 6 post 3$^{rd}$ vaccination to measure Anti-HBs IgG1 and Anti-HB IgG2 by ELISA as follows.

Anti-HBs IgG1: 96 well plates were coated overnight at 4° C., with recombinant Hepatitis B Surface antigen Protein, Abcam (0.25 µg/mL in DPBS). On the following day, plates were blocked with 10% goat sera in ELISA wash buffer (0.05% Tween-20 in PBS) for 1 hour at 37° C. Plates were washed with wash buffer, followed by addition of 2-fold dilutions of individual mouse sera; starting at 1:10,000 to 1:1280,000. Plates were incubated, for 1.5 hours at 37° C., followed by plate washing and addition of secondary antibody. Goat anti-mouse IgG1 (Bethyl), diluted 1:10,000 in 10% goat sera in ELISA wash buffer was added and the plates were incubated for 1.5 hours at 37° C. TMB One component Microwell substrate was added to the plates, incubated at room temperature for 10 minutes and then Stop solution was added. Absorbance was read at 450 nm using a MAXline plate reader.

Anti-HBs IgG2a: 96 well plates were coated overnight at 4° C., with Recombinant Hepatitis B Surface antigen Protein, Abcam (0.25 µg/ml in DPBS). On the following day, plates were blocked with 10% goat sera in ELISA wash buffer, for 1 hour at 37° C. Plates were washed with wash buffer, followed by addition of 2-fold dilutions, of individual mouse sera; starting at 1:5,000 to 1:640,000. Plates were incubated, for 1.5 hours at 37° C., followed by plate washing and addition of secondary antibody. Goat anti-mouse IgG2a (Bethyl), diluted 1:10,000 in 10% goat sera in ELISA wash buffer was added and the plates were incubated for 1.5 hours at 37° C. TMB One component Microwell substrate was added to the plates and incubated at room temperature for 10 minutes and then Stop solution was added. Absorbance was read at 450 nm using a MAXline plate reader.

The results are shown in Table 6 below.

TABLE 6

Individual Ig G1/IgG2 Ratios

| Individual Mouse number | Ratio IgG1/IgG2a 10 µg HBsAg Formulation containing 500 µg/mL[Al+++] (Alhydrogel) | Ratio IgG1/IgG2a 20 µg HBsAg Formulation containing 500 µg/mL [Al+++] (Adjuphos) |
|---|---|---|
| 1 | 5.3 | 2.5 |
| 2 | 36.5 | 3.6 |
| 3 | 118.3 | 5.6 |
| 4 | 19.9 | 0.1 |
| 5 | 35.9 | 6.9 |
| 6 | 2.0 | 4.6 |
| 7 | 20.5 | 0.9 |
| 8 | N/A | 9.4 |

As can be seen from Table 6, the immunogenic composition of the disclosure containing 20 µg HBsAg and 500 µg/ml aluminum as aluminum phosphate adjuvant stimulates a significantly lower ratio of IgG1 to IgG2a. Since IgG2a stimulation is a marker for Th1 activity, this altered ratio indicates that the composition containing 20 µg HBsAg and 500 µg/ml aluminum as aluminum phosphate adjuvant elicits a stronger Th1 response than the composition comprising 20 µg HBsAg and 500 µg/ml aluminum as aluminum phosphate adjuvant.

Example 6: Dose Ranging Study in Mice Following Vaccination with a Commercially Available Prophylactic Vaccine Known as Sci-B-Vac (10 µg/ml HBsAg Comprising S, Pre-S1 and Pre-S2 and 500 µg/ml Aluminum as Aluminum Hydroxide Adjuvant) and Three Different Doses of the Composition of the Disclosure Comprising 20 µg, 40 µg and 60 Ug HBsAg and 500 µg/ml Aluminum as Aluminum Phosphate Adjuvant This Example describes a dose ranging study which examines the Th1 activity in mice following vaccination with the commercially available prophylactic vaccine known as Sci-B-Vac which comprises 10 µg/ml HBsAg comprising S, Pre-S1 and Pre-S2 proteins and 500 µg/mL aluminum as aluminum hydroxide adjuvant (TA6 in Table 3) and three different doses comprising of the same HBsAg immunogenic composition of the disclosure and 500 µg/mL aluminum as aluminum phosphate adjuvant. The three different doses were as follows HBsAg (20 µg/ml) (TA11 in Table 3); HBsAg (40 µg/ml) (TA10 in Table 3) and HBsAg (60 µg/ml) (TA 13 in Table 3).

Briefly, Balb/c mice (n=8/group) were vaccinated intramuscularly 3 times, 3 weeks apart with a mouse dose of each the compositions, specifically 3 µg, 2 µg and 1 µg. Splenocytes were harvested from mice 7 days after the $3^{rd}$ vaccination and stimulated with overlapping peptide pools specific to preS1, Pre-S2, and HBsAg. The IFN-γ-secreting T cell responses were evaluated by ELISPOT after 48 hours of culture as follows. One day prior to spleen collection and processing, ELISpot plates (Millipore) were coated with 100 µl Interferon-gamma (IFN-γ) capture antibody at a concentration of 15 µg/mL (Mabtech) and incubated overnight at 4° C.

On the day of spleen collection and processing, the coated ELISpot plates were washed 5 times with 200 µl sterile PBS and blocked with 100 µl of R10 media for 1-2 hrs. Once the splenocytes had been isolated and counted, the R10 blocking media was removed and 50 µl of splenocytes (300,000 cells) and 50 µl of the stimulants were plated onto the ELISpot assay plates. Splenocytes from each mouse were stimulated in duplicate with following stimulants: PreS1 (final stimulation concentration=13.5 µg/ml), Pre-S2 (final stimulation concentration=5.5 µg/ml) and HBsAg (final stimulation concentration=27 µg/mL), R10 as a negative control and phorbol 12-myristate 13-acetate and ionomycin (PMA (20 ng/ml)/Ionomycin (1 µg/ml) as a positive control. The ELISpot plates were then placed into a humid 37° C. with 5% CO2 incubator for 40-48 hours. After incubation, the plates were washed 5 times with 200 µl PBS-Tween for removal of splenocytes, stimulants and media and 100 µl of IFN-γ capture antibody (Mabtech) at a concentration of 1 µg/ml was then added to each well. Following a 2 hour incubation, the ELISpot plates were washed 5 times with PBC-Tween and 100 µl streptomycin horseradish peroxidase (strep-HRP) diluted 1:1000 was added to each well. The plates were then incubated for a further hour before being developed for 30 minutes at room temperature by adding 100 µL 3-Amino-9-ethylcarbazole (AEC) substrate (BD BioSciences). The observed spots were counted by ZellNet Consulting and the final data reported as spot forming units (SFC) per one million splenocytes. The Th1 activity of the different compositions as measured by ELISPOT are shown in Table 7.

TABLE 7

| | Th1 Activity as Measured by ELISPOT | | | | | |
|---|---|---|---|---|---|---|
| Immunogenic | Pre-S1 (IFN-γ + SFC/$10^6$ splenocytes) | | Pre-S2 (IFN-γ + SFC/$10^6$ splenocytes) | | sAg (IFN-γ + SFC/$10^6$ splenocytes) | |
| Composition | M | SE | M | SE | M | SE |
| 20 µg HBsAg Formulation containing 500 µg/mL[Al+++] (Adjuphos) | 1.665 | 1.044 | 261.2 | 62.43 | 498.0 | 125.4 |
| 40 µg HBsAg Formulation containing 500 µg/mL[Al+++] (Adjuphos) | 0.9514 | 0.4951 | 222.6 | 69.20 | 649.6 | 109.1 |
| 60 µg HBsAg Formulation containing 500 µg/mL[Al+++] (Adjuphos) | 0.7136 | 0.7136 | 148.9 | 31.01 | 422.0 | 102.0 |
| 10 µg HBsAg Formulation containing 500 µg/mL[Al+++] (Alhydrogel) | 0.0 | 0.0 | 108.4 | 36.95 | 226.4 | 28.54 |

As can be seen in Table 7, the 20 µg and 40 µg and 60 µg dose of the compositions comprising HBsAg comprising S, Pre-S1 and Pre-S2 proteins and 500 µg/mL aluminum as aluminum phosphate adjuvant were able to elicit greater numbers of Pre-S2 and HBsAg specific IFN-γ-secreting T cells by ELISPOT when compared to the 10 µg/ml HBsAg comprising S, Pre-S1 and Pre-S2 proteins and 500 µg/mL aluminum as aluminum hydroxide adjuvant (TA6 in Table 3). Accordingly, each of the three doses of the immunogenic compositions of the disclosure induced a higher T cell response that the composition comprising 10 µg/ml HBsAg comprising S, Pre-S1 and Pre-S2 proteins and 500 µg/mL aluminum as aluminum hydroxide adjuvant.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

What is claimed is:

1. An immunogenic composition comprising:
    (a) an HBsAg antigen comprising S protein, Pre-S1 protein and Pre-S2 protein; and
    (b) an aluminum phosphate adjuvant,
    wherein the composition comprises at least 20 μg/ml of HBsAg antigen and the amount of non-adsorbed antigen is at least 30%.

2. The immunogenic composition of claim 1 wherein the aluminum is present in a concentration of 500 μg/ml.

3. The immunogenic composition of claim 1 wherein the HBsAg antigen is present in a concentration of 20 μg/ml.

4. The immunogenic composition of claim 1 wherein the HBsAg antigen is present in a concentration of 40 μg/ml.

5. The immunogenic composition of claim 1 wherein the HBsAg antigen is present in a concentration of 60 μg/ml.

6. The immunogenic composition of claim 1 for use inducing a Th1 cell response in a mammal.

7. Use of the immunogenic composition of claim 1 for manufacture of a drug for inducing a Th1 cell response in a subject.

8. The use of claim 7 wherein the subject has been infected with Hepatitis B.

9. A pharmaceutical composition comprising the immunogenic composition of claim 1 and a pharmaceutically acceptable excipient.

10. The pharmaceutical composition of claim 9 for use in treating a subject suffering from Hepatitis B.

11. A method of inducing a Th1 cell response in a mammal, said method comprising administering the immunogenic composition of claim 1.

12. A method of treating Hepatitis B in a subject, said method comprising administering a therapeutically effective amount of the immunogenic composition of claim 1 to the subject.

13. The method of claim 12 wherein an additional Hepatitis B treatment is administered to the subject prior to, concurrently with, or after administration of the immunogenic composition to the subject.

14. The method of claim 13 wherein the additional Hepatitis B treatment is a nucleoside inhibitor or a pegylated interferon alpha.

15. The method of claim 13 wherein the additional Hepatitis B treatment is a polymerase inhibitor, an RNase H inhibitor, a TLR agonist, an N-glycosylation inhibitor, an antisense oligonucleotide, an anti-hepatitis B antibody, a capsid inhibitor, a core protein inhibitor, a core assembly modulator, an S-antigen reducer or sequesterer, a nucleic acid polymers, a ccc DNA inhibitor, an interferon, an immune modulator or an siRNA.

* * * * *

SEQUENCE LISTING

<160> NUMBER OF SEQ ID NOS: 3

<210> SEQ ID NO 1
<211> LENGTH: 226
<212> TYPE: PRT

-continued

<213> ORGANISM: Artificial Sequence
<220> FEATURE:
<223> OTHER INFORMATION: Description of Artificial Sequence: Synthetic
      polypeptide

<400> SEQUENCE: 1

Met Glu Asn Ile Thr Ser Gly Phe Leu Gly Pro Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ser Pro Val Cys
            35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65              70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Thr Thr Thr Ser Thr Gly Pro Cys Lys Thr Cys Thr Thr Pro Ala
                115                 120                 125

Gln Gly Asn Ser Met Phe Pro Ser Cys Cys Cys Thr Lys Pro Thr Asp
                130                 135                 140

Gly Asn Cys Thr Cys Ile Pro Ile Pro Ser Ser Trp Ala Phe Ala Lys
145                 150                 155                 160

Tyr Leu Trp Glu Trp Gly Ser Val Arg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Asn Leu Tyr Asn Ile
                195                 200                 205

Leu Ser Pro Phe Ile Pro Leu Leu Pro Ile Phe Phe Cys Leu Trp Val
    210                 215                 220

Tyr Ile
225

<210> SEQ ID NO 2
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Trp Asn Ser Thr Ala Phe His Gln Ala Leu Gln His Pro Arg
1               5                   10                  15

Val Arg Gly Leu Tyr Phe Pro Ala Gly Gly Ser Ser Ser Gly Thr Val
                20                  25                  30

Asn Pro Ala Gln Asn Ile Ala Ser His Ile Ser Ser Ile Ser Ser Arg
            35                  40                  45

Thr Gly Asp Pro Ala Pro Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe

```
            85                  90                  95
Leu Gly Gly Ser Pro Val Cys Leu Gly Gln Asn Ser Gln Ser Pro Thr
            100                 105                 110

Ser Asn His Ser Pro Thr Ser Cys Pro Pro Ile Cys Pro Gly Tyr Arg
            115                 120                 125

Trp Met Cys Leu Arg Arg Phe Ile Ile Phe Leu Phe Ile Leu Leu Leu
            130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Thr Thr Thr Ser Thr Gly Pro Cys
                165                 170                 175

Lys Thr Cys Thr Thr Pro Ala Gln Gly Asn Ser Met Phe Pro Ser Cys
            180                 185                 190

Cys Cys Thr Lys Pro Thr Asp Gly Asn Cys Thr Cys Ile Pro Ile Pro
            195                 200                 205

Ser Ser Trp Ala Phe Ala Lys Tyr Leu Trp Glu Trp Gly Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Asn Leu Tyr Asn Ile Leu Ser Pro Phe Ile Pro Leu Leu Pro
            260                 265                 270

Ile Phe Phe Cys Leu Trp Val Tyr Ile
            275                 280

<210> SEQ ID NO 3
<211> LENGTH: 399
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Leu Ser Trp Thr Val Pro Leu Glu Trp Gly Lys Asn Gln Ser
1               5                   10                  15

Thr Ser Asn Pro Leu Gly Phe Phe Pro Asp His Gln Leu Asp Pro Ala
            20                  25                  30

Phe Gly Ala Asn Ser Asn Asn Pro Asp Trp Asp Leu Asn Ser Asn Lys
        35                  40                  45

Asp His Trp Pro Gln Ala Asn Gln Val Gly Val Gly Ala Phe Gly Pro
    50                  55                  60

Gly Phe Thr Pro Pro His Gly Gly Leu Leu Gly Trp Ser Ser Gln Ala
65                  70                  75                  80

Gln Gly Thr Leu His Thr Val Pro Ala Val Pro Pro Ala Ser Thr
                85                  90                  95

Asn Arg Gln Thr Lys Arg Gln Pro Thr Pro Ile Ser Pro Pro Leu Arg
            100                 105                 110

Asp Ser His Pro Gln Ala Met Gln Trp Asn Ser Thr Ala Phe His Gln
            115                 120                 125

Ala Leu Gln His Pro Arg Val Arg Gly Leu Tyr Phe Pro Ala Gly Gly
            130                 135                 140

Ser Ser Ser Gly Thr Val Asn Pro Ala Gln Asn Ile Ala Ser His Ile
145                 150                 155                 160
```

```
                    -continued

Ser Ser Ile Ser Ser Arg Thr Gly Asp Pro Ala Pro Asn Met Glu Asn
            165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
            195                 200                 205

Trp Thr Ser Leu Asn Phe Leu Gly Gly Ser Pro Val Cys Leu Gly Gln
            210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
            245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Ile Pro Gly Ser Thr Thr
            275                 280                 285

Thr Ser Thr Gly Pro Cys Lys Thr Cys Thr Thr Pro Ala Gln Gly Asn
            290                 295                 300

Ser Met Phe Pro Ser Cys Cys Cys Thr Lys Pro Thr Asp Gly Asn Cys
305                 310                 315                 320

Thr Cys Ile Pro Ile Pro Ser Ser Trp Ala Phe Ala Lys Tyr Leu Trp
                325                 330                 335

Glu Trp Gly Ser Val Arg Phe Ser Trp Leu Ser Leu Leu Val Pro Phe
            340                 345                 350

Val Gln Trp Phe Val Gly Leu Ser Pro Thr Val Trp Leu Ser Val Ile
            355                 360                 365

Trp Met Met Trp Tyr Trp Gly Pro Asn Leu Tyr Asn Ile Leu Ser Pro
            370                 375                 380

Phe Ile Pro Leu Leu Pro Ile Phe Phe Cys Leu Trp Val Tyr Ile
385                 390                 395
```